(12) United States Patent
Neeves et al.

(10) Patent No.: US 8,486,349 B2
(45) Date of Patent: Jul. 16, 2013

(54) MICROFLUIDIC FLOW ASSAY FOR MEASURING HEMOSTATIC PHENOTYPES

(75) Inventors: Keith Benjamin Neeves, Denver, CO (US); Ryan R. Hansen, Denver, CO (US)

(73) Assignee: Colorado School of Mines, Golden, CO (US)

( * ) Notice: Subject to any disclaimer, the term of this patent is extended or adjusted under 35 U.S.C. 154(b) by 0 days.

(21) Appl. No.: 13/045,404

(22) Filed: Mar. 10, 2011

(65) Prior Publication Data

US 2011/0223627 A1 Sep. 15, 2011

Related U.S. Application Data

(60) Provisional application No. 61/313,257, filed on Mar. 12, 2010.

(51) Int. Cl.
*B01L 3/00* (2006.01)

(52) U.S. Cl.
USPC ........... 422/502; 422/52; 422/63; 422/64; 422/82.05; 422/82.08; 422/82.09; 422/82.11; 422/407; 422/425; 422/426; 422/429; 422/500; 422/501; 422/503; 422/504; 435/164; 435/165; 435/283.1; 435/286.4; 435/287.1; 435/287.2; 435/288.5; 435/288.7; 435/4; 435/5; 435/6.11; 435/6.12; 435/6.19; 435/7.1; 435/7.2; 435/7.9; 435/29; 436/43; 436/52; 436/53; 436/149; 436/164; 436/165; 436/166; 436/172; 436/174; 436/180; 436/518; 436/524; 436/805

(58) Field of Classification Search
USPC ............. 422/52, 63, 64, 82.05, 82.08, 82.09, 422/82.11, 407, 425, 426, 429, 500, 501, 422/502, 503, 504; 435/164, 165, 283.1, 435/286.4, 287.1, 287.2, 288.5, 288.7, 4, 435/5, 6.11, 6.12, 6.19, 7.1, 7.2, 7.9, 29; 436/43, 436/52, 53, 149, 164, 165, 166, 172, 174, 436/180, 518, 524, 805, 807, 809; 204/403.01, 204/450; 356/450; 506/3, 7, 9, 10, 32, 39
See application file for complete search history.

(56) References Cited

U.S. PATENT DOCUMENTS 7,318,902 B2   1/2008 Oakey et al.

OTHER PUBLICATIONS

Okorie "Determination of surface tissue factor thresholds that trigger coagulation at venous and arterial shear rates: amplification of 100 fM circulating tissue factor requires flow" Blood, Apr. 1, 2008, vol. 111, No. 7, pp. 3507-3513).*
Neeves et al "Microfluidic focal thrombosis model for measuring murine platelet deposition and stability: PAR4 signaling enhances shear-resistance of platelet aggregates" Journal of Thrombosis and Haemostasis, 6: 2193-2201.*
Shen et al "Using microfluidics to understand the effect of spatial distribution of tissue factor on blood coagulation" Thrombosis Research (2008) 122 Suppl. 1, S27-S30).*

(Continued)

*Primary Examiner* — Dennis M White
(74) *Attorney, Agent, or Firm* — Sheridan Ross P.C.

(57) ABSTRACT

A microfluidic-based flow assay and methods of manufacturing the same are provided. Specifically, the microfluidic flow assay includes a micropatterned surface that induces clot formation and an array of microfluidic channels though which blood flows. The micropatterned surface contains two clotting stimuli, one for inducing platelet adhesion and another for inducing the coagulation cascade.

20 Claims, 9 Drawing Sheets

OTHER PUBLICATIONS

Kastrup et al. "Modular chemical mechanism predicts spatiotemporal dynamics of initiation in the complex network of hemostasis," PNAS, Oct. 2006, vol. 103, No. 43, pp. 15747-15752.

Kastrup et al. "Characterization of the Threshold Response of Initiation of Blood Clotting to Stimulus Patch Size," Biophysical Journal, Oct. 2007, vol. 93, pp. 2969-2977.

Runyon et al. "Propagation of Blood Clotting in the Complex Biochemical Network of Hemostasis is Described by a Simple Mechanism," Journal of the American Chemical Society, Jun. 2007, vol. 129, No. 22, pp. 7014-7015.

Runyon et al. "Effects of Shear Rate on Propagation of Blood Clotting Determined Using Microfluidics and Numerical Simulations," Journal of the American Chemical Society, Mar. 2008, vol. 130, No. 11, pp. 3458-3464.

Shen et al. "Threshold Response of Initiation of Blood Coagulation by Tissue Factor in Patterned Microfluidic Capillaries is Controlled by Shear Rate," Arteriosclerosis, Thrombosis, and Vascular Biology, Nov. 2008, vol. 28, No. 11, pp. 2035-2041.

Shen et al. "Confinement Regulates Complex Biochemical Networks: Initiation of Blood Clotting by "Diffusion Acting"," Biophysical Journal, Oct. 2009, vol. 97, pp. 2137-2145.

* cited by examiner

MICROFLUIDIC FLOW ASSAY FOR MEASURING HEMOSTATIC PHENOTYPES

CROSS-REFERENCE TO RELATED APPLICATIONS

This application claims the benefit of U.S. Provisional Patent Application Ser. No. 61/313,257, filed Mar. 12, 2010, the entire disclosure of which is hereby incorporated herein by reference.

FIELD OF INVENTION

The invention relates to a microfluidic-based flow assay for use in analyzing bleeding and thrombotic disorders, dosing anticoagulant and antiplatelet drugs, tracking the effects of pharmacological interventions on thrombosis, and methods of making the same.

BACKGROUND OF INVENTION

Maintaining the balance between bleeding and thrombosis remains one of the greatest challenges facing the biomedical community. Excessive bleeding is an important medical issue. For example, post partum bleeding represents a leading cause of maternal mortality and causes serious morbidity in developing countries. Individuals with genetic bleeding disorders, such as hemophilia, have a decreased ability to clot blood because of deficiencies in certain coagulation factors.

On the other end of the spectrum, excessive clotting, or thrombosis, is a major complication of surgery and is integrally involved in atherosclerosis, obesity, infection, diabetes, cancer, and autoimmune disorders. Over the last decade, significant advances have been made in understanding the molecular basis of bleeding and thrombotic disorders; however, a large portion of the observed variability remains unknown.

Parallel with these discoveries, there has been a rapid development of new drugs like recombinant proteins for replacement and interventional therapies. Interestingly, what remains strikingly deficient in clinical hematology are techniques to diagnose a very broad range of disorders of both deficient and excessive clotting as well as to monitor the effects of therapeutic interventions.

Diagnosing the severity of bleeding disorder is impossible with current bleeding assays, particularly because most current bleeding assays test for either platelet function or coagulation, but not both. Thus, most existing solutions do not properly create an environment which properly simulates a natural human wound or point of bleeding. In addition, most of these conventional assays occur under static, or no flow, conditions. Since blood is a moving fluid, however, there are several advantages to studying it under flow in bleeding diagnostics.

SUMMARY OF INVENTION

It is, therefore, one aspect of the present invention to provide a device which contains two clotting stimuli, one for inducing platelet adhesion and another for inducing the coagulation cascade.

It is another aspect of the present invention to provide a device which allows blood to flow over a micro-patterned surface which induces clot formation. In some embodiments, a microfluidic channel is provided with one or more clot inducing areas. Each of the one or more clot inducing areas may include a micro-patterned surface that induces clot formation via two different stimuli (e.g., inducing platelet adhesion and inducing coagulation).

It is another aspect of the present invention to combine the physics of blood flow and the biology of the clotting system into a single device.

In accordance with at least some embodiments of the present invention, a microfluidic flow assay is provided which accounts for the three main factors which contribute to the formation of a blood clot: platelets, coagulation, and blood flow.

Platelets are the first responders to a vascular injury. A vascular injury can be due to trauma or the rupture of an atherosclerotic plaque. Platelets adhere to proteins, especially collagens, found underneath the cells that line blood vessels and von Willebrand factor, which is secreted by endothelial cells and platelets. Following platelet adhesion, a series of enzymatic reactions occur that are collectively known as the coagulation cascade. The main catalyst for the coagulation cascade is a transmembrane protein called tissue factor.

Embodiments of the present invention provide a microfluidic device having a clot inducing area in a microfluidic channel though which blood is allowed to flow, where the clot inducing area includes a mixture of collagen, von Willebrand factor, and tissue factor. In some embodiments, the area(s) of tissue factor which are exposed to blood flowing thereby are interspersed in the collagen in a predetermined pattern.

Because there is significant variability in clotting factors and blood cell counts in the healthy population, it is useful to provide a microfluidic device in which the microfluidic channel(s) and clot inducing areas, which are also referred to as prothrombotic surfaces, are homogeneous and repeatable. Otherwise, it may become difficult to determine whether differences in platelet and fibrin accumulation are variations in blood constituent or variability in the prothrombotic surface. It is, therefore, another aspect of the present invention to standardize the methods for patterning molecules that stimulate these two mechanisms and evaluate the microfluidic flow assay in a clinical setting. More specifically, embodiments of the present invention provide a homogeneous, repeatable collagen patterning method for measuring platelet adhesion. Embodiments of the present invention also provide a repeatable method for co-patterning collage and tissue factor for measuring coagulation defects.

It is another aspect of the present invention to provide a flow assay which allows the in vitro study of platelet response to defined surfaces at controlled wall shear stresses (e.g., via use of a microfluidic channel).

In accordance with at least some embodiments of the present invention, a microfluidic device is provided which generally comprises:

at least one microfluidic channel; and at least one prothrombotic surface provided in the at least one microfluidic channel, wherein the at least one prothrombotic surface is capable of inducing both platelet adhesion and coagulation cascade.

In accordance with at least some embodiments of the present invention, a method of manufacturing a microfluidic device is provided which generally comprises:

providing a substrate;

creating at least one prothrombotic surface on the substrate, wherein the at least one prothrombotic surface is capable of inducing both platelet adhesion and coagulation cascade; and establishing at least one microfluidic channel which intersects at least a portion of the at least one prothrombotic surface.

In accordance with at least some embodiments of the present invention, a microfluidic device made by the above-described method is also provided.

In accordance with at least some embodiments of the present invention, a microfluidic channel through which blood is capable of flowing is provided that generally comprises:

at least one prothrombotic surface provided as a part of at least a portion of one surface in the channel, wherein the at least one prothrombotic surface is capable of inducing both platelet adhesion and coagulation cascade in the blood.

In accordance with at least some embodiments of the present invention, a kit for measuring clot formation is provided which generally comprises:

a vacuum or hemetically sealed microfluidic device, the microfluidic device comprising at least one microfluidic channel and at least one prothrombotic surface provided in the at least one microfluidic channel, wherein the at least one prothrombotic surface is capable of inducing both platelet adhesion and the coagulation cascade.

In accordance with at least some embodiments of the present invention, a method of measuring clot formation or clotting characteristics is provided which generally comprises:

causing blood to flow through a microfluidic channel under laminar flow conditions, wherein the blood flows through the microfluidic channel and across at least one prothrombotic surface provided in the microfluidic channel, wherein the at least one prothrombotic surface is capable of inducing both platelet adhesion and coagulation cascade; and analyzing, around the at least one prothrombotic surface, a number of blood cells which have substantially stopped flowing.

DETAILED DESCRIPTION

Embodiments of the present invention will now be described in connection with methods, devices, and systems used for testing blood clotting or determining whether an individual is prone to blood-clotting issues. However, those skilled in the art will appreciate that embodiments of the present invention are not limited to the field of blood flow and can be utilized in other fields without departing from the scope of the present invention.

Figure 1:
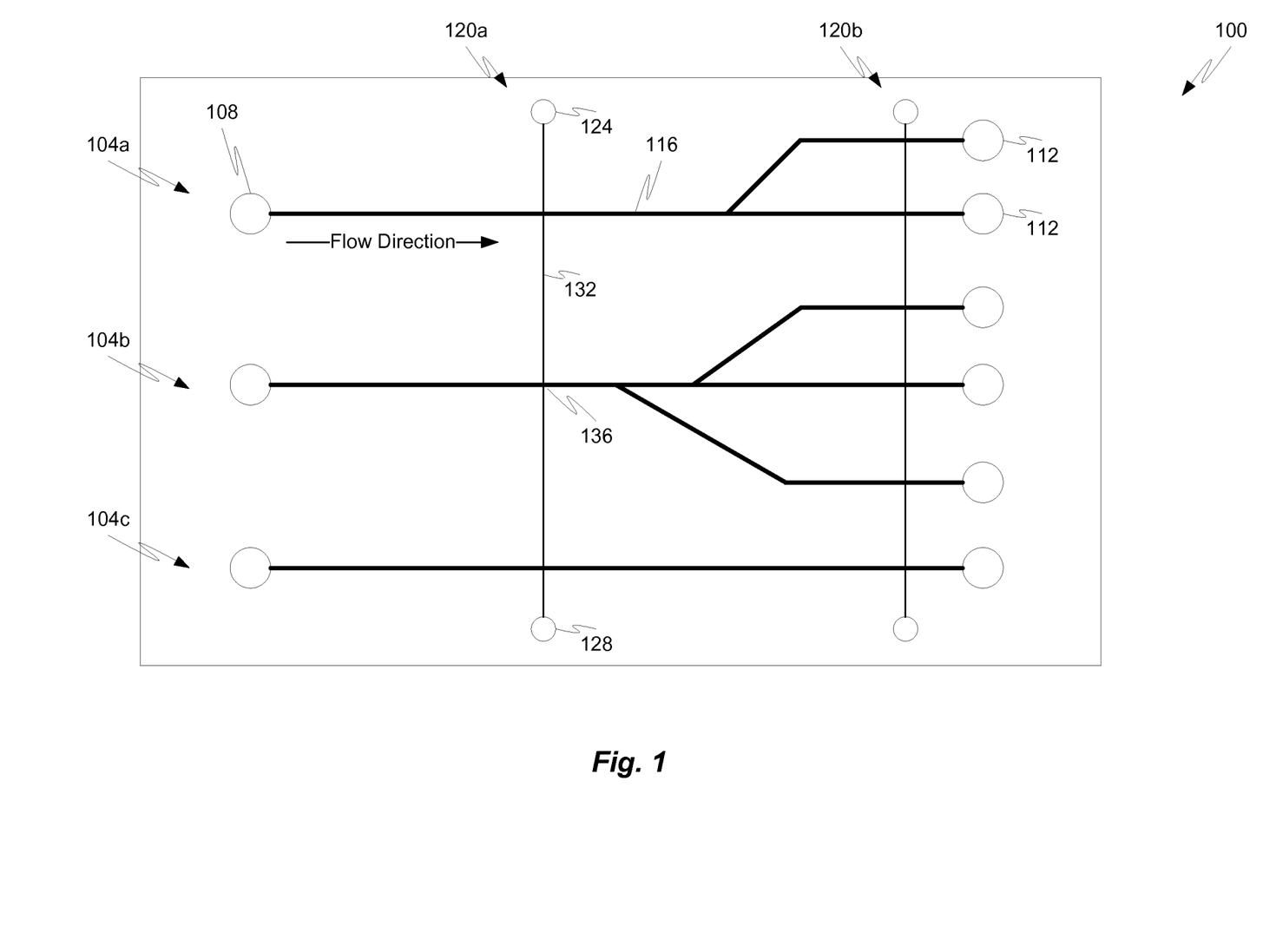
FIG. 1 depicts a top view of an exemplary microfluidic device in accordance with at least some embodiments of the present invention.

Referring initially to FIG. 1, an exemplary microfluidic device 100 will be described in accordance with at least some embodiments of the present invention. More specifically, the microfluidic device 100 may include a plurality of fluid-receiving passages 104*a*, 104*b*, 104*c*, which are capable of receiving fluid at a receiving end 108 and allowing said fluid to flow through a microfluidic channel 116 to a terminal end 112.

In accordance with at least some embodiments of the present invention, the fluid flowing through the microfluidic channel 116 may be blood, such as human blood. Additional details of microfluidic channels which facilitate laminar flow conditions are described, for example, in U.S. Pat. No. 7,318,902 to Oakey et al., the entire contents of which are hereby incorporated herein by reference.

Although three receiving ends 108 are depicted, one skilled in the art will appreciate that one or more of the microfluidic channels 116 may split into multiple channels, thereby resulting in a number of terminal ends 112 which exceeds the number of receiving ends 108. As can be appreciated by one skilled in the art, however, the number of receiving ends 108 may equal the number of terminal ends 112. The configuration and design of the microfluidic channels 116 can vary without departing from the scope of the present invention.

In addition to comprising microfluidic channels 116, the microfluidic device 100 may also comprise one or more prothrombotic structures 120*a*, 120*b* which intersect one or more of the microfluidic channels 116. In particular, a prothrombotic structure 120*a*, 120*b* include a first end 124, a second end 128, and a prothrombotic surface 132 therebetween. The prothrombotic surface 132 may intersect the microfluidic channel 116 at an area of intersection generally referred to as a clot forming area 136. This clot forming area 136 is an area within the microfluidic channel 116 in which both platelet adhesion and coagulation cascade is induced in the blood flowing through the microfluidic channel 116.

Figure 2A:
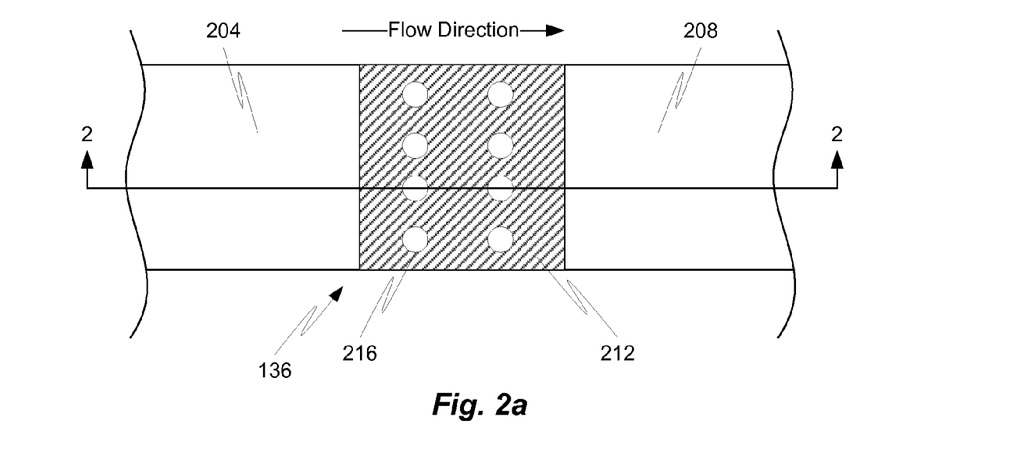
FIG. 2*a* depicts an exploded top view of a portion of an exemplary microfluidic channel in accordance with at least some embodiments of the present invention.

The specific properties of the prothrombotic surface 132 which induce both platelet adhesion and coagulation cascade will now be described in connection with FIGS. 2*a* and 2*b*. In particular, the clot forming area 136 is depicted in further detail in FIGS. 2*a* and 2*b*. In accordance with at least some embodiments of the present invention, the prothrombotic surface 132 includes collagen 212 or a similar material known to induce platelet adhesion. The prothrombotic surface 132 may also include structures of tissue factor 216, which are designed to induce the coagulation cascade. By providing the prothrombotic surface 132 with both collagen 212 and tissue factor 216, the prothrombotic surface 132 is capable of inducing both platelet adhesion and coagulation cascade in blood flowing through the microfluidic channel 116 when the blood traverses the clot forming area 136.

Surrounding the clot forming area 136 in the microfluidic channel 116 are a first 204 and second 208 passive surface, which may or may not include endothelial cells, and which is generally neutral with respect to inducing blood clotting. Accordingly, the amount of blood clotting induced within the microfluidic channel 116 can be tightly controlled by precisely controlling the size of the prothrombotic surface 132 and the amount of tissue factor 216 provided therein.

In accordance with at least some embodiments of the present invention, the first 204 and second 208 surface may be considered a neutral or passivated surface. In some embodiments, a lipid is used for the first 204 and second 208 surface. In particular, a bovine serum albumin (BSA) may be utilized as a passivity protein. This particular protein is known not to induce any type of blood clotting, such as platelet adhesion or the coagulation cascade.

The width of the prothrombotic surface 132 may vary depending upon desired clotting or the size of the microfluidic channel 116 (e.g., cross-sectional area of the microfluidic channel 116). In some embodiments, the width of the prothrombotic surface 132 may be about 100 microns. This may be a particularly useful size of prothrombotic surface 132 if the microfluidic channel 116 comprises a cross sectional area of about 50 microns×250 microns. This particular geometry is useful because it provides an area of constant shear stress across the middle of the channel 116. As can be appreciated by one skilled in the art, however, the actual width of the prothrombotic surface 132 can have a greater or lesser size without departing from the scope of the present invention.

The structures of tissue factor 216 may comprise any type of shape. For example, although the structures of tissue factor 216 are depicted as having a generally circular cross-section, the structures of tissue factor 216 may comprise a square cross-section, oval cross-section, rectangular cross-section, or unshaped cross-section. In some embodiments, a circular cross-section tissue factor 216 may comprise a diameter of between 10-100 microns. Smaller or larger structures of tissue factor 216 may be used. It should be noted that a 10 micron diameter island of tissue factor 216 substantially represents a single cell in a human. Thus, utilization of a structure of tissue factor 216 having a diameter of about 10 microns may be preferable for modeling a typical human bleeding environment. Additionally, the number of structures of tissue factor 216 provided in the clot forming area 136 can be any number larger than one and the distribution of the structures of tissue factor 216 within the collagen can either be symmetrical, asymmetrical, or random. As one exemplary distribution, lanes of tissue factor 216 may be provided in the clot forming area 136 that traverse substantially the length of the clot forming area 136 but do not traverse the width of the clot forming area 136. The lanes of tissue factor 216 may be separated by non-tissue factor lanes.

Moreover, the ratio of collagen 212 surface area to tissue factor 216 surface area in a given prothrombotic surface 132 is less than 1:1. In more preferred embodiments, there is at least a 2:1 ratio of collage 212 surface area to tissue factor 216 surface area, meaning that for every square nm of tissue factor 216 exposed there is at least two square nm of collagen 212 exposed. This ratio can also vary according to conditions and the size of the microfluidic channel 216 without departing from the scope of the present invention.

In accordance with at least some embodiments of the present invention, the collagen 212 is constructed of a fibrillar type 1 collagen. In some embodiments, an equine or rat tail-based collagen can be used. In certain embodiments where a tighter control on variables within the microfluidic device 100 is required, an acid soluble collagen having a more homogeneous surface than a non-acid soluble collagen can be utilized. For example, rat tail digested in a pH 3 environment can be utilized as a purer form of collagen than a non-treated collagen.

In accordance with at least some embodiments of the present invention, the structures of tissue factor 216 can be constructed of a lipid or lipid membrane that is used as an expressed surface of "activated" cells. This creates a significant amount of a molecule known as thrombin when blood plasma interacts with the lipid. Thrombin is a known serine protease that creates a biopolymer of fibrin by cleaving fibrinopeptide from the plasma protein fibrinogen. Fibrin forms a highly entangled hydrogel that provides the scaffold onto which a blood clot grows. Generally speaking, high concentrations of thrombin are created during via the extrinsic or tissue factor pathway of the coagulation cascade; this is why tissue factor is known as a coagulation cascade inducing agent.

Figure 2B:
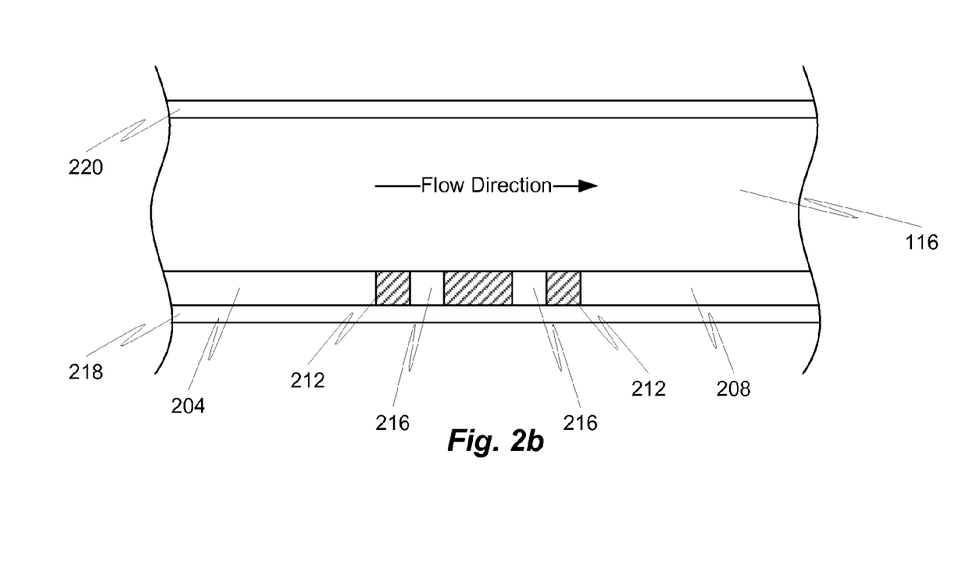
FIG. 2*b* depicts an exploded partial cross-sectional view across line 2-2 of an exemplary microfluidic channel in accordance with at least some embodiments of the present invention.

As can be seen in FIG. 2b, the first 204 and second 208 areas of neutral material as well as the prothrombotic surface 132 (comprising the layer of collagen 212 and structures of tissue factor 216) may be provided on a substrate 218. Additionally, the microfluidic channel 116 may be enclosed with a lid or top layer 220. In some embodiments the substrate 218 and/or lid or top layer 220 is constructed of polydimethylsiloxane (PDMS) or a similar type of silicone. As an alternative, or in addition, the substrate 218 and/or lid or top layer 220 is constructed of glass, plastic, gold, combinations thereof, or any other type of known substrate material used in surface chemistry.

Figure 3:
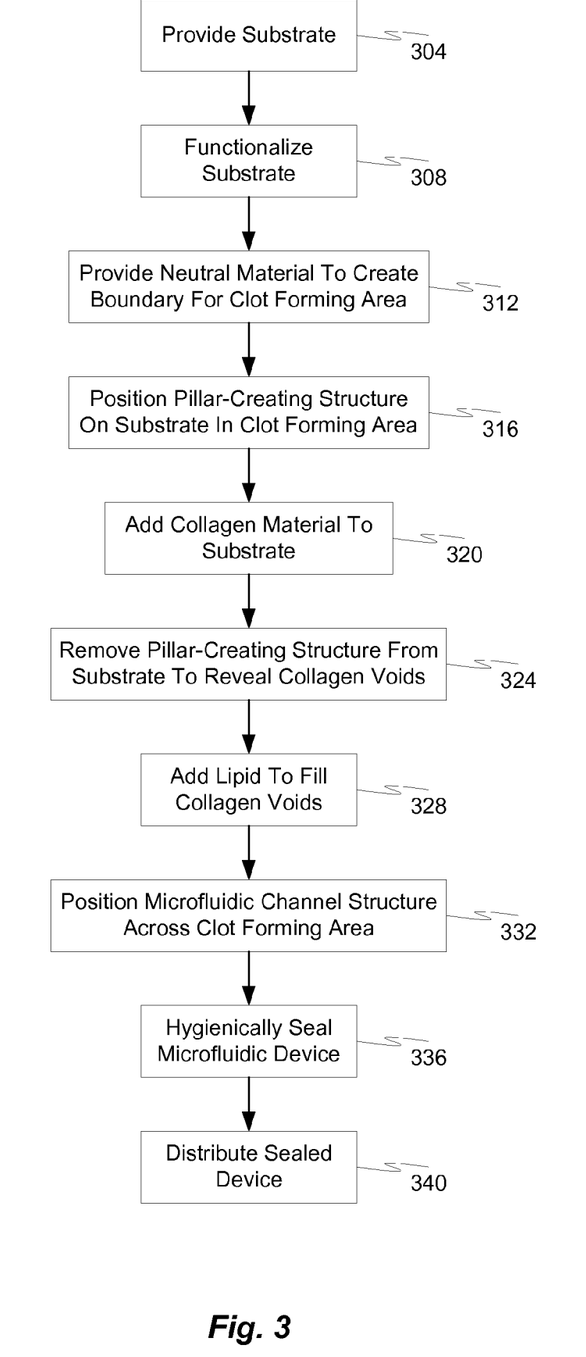
FIG. 3 depicts an exemplary method of manufacturing a microfluidic device in accordance with at least some embodiments of the present invention.
Figure 4:
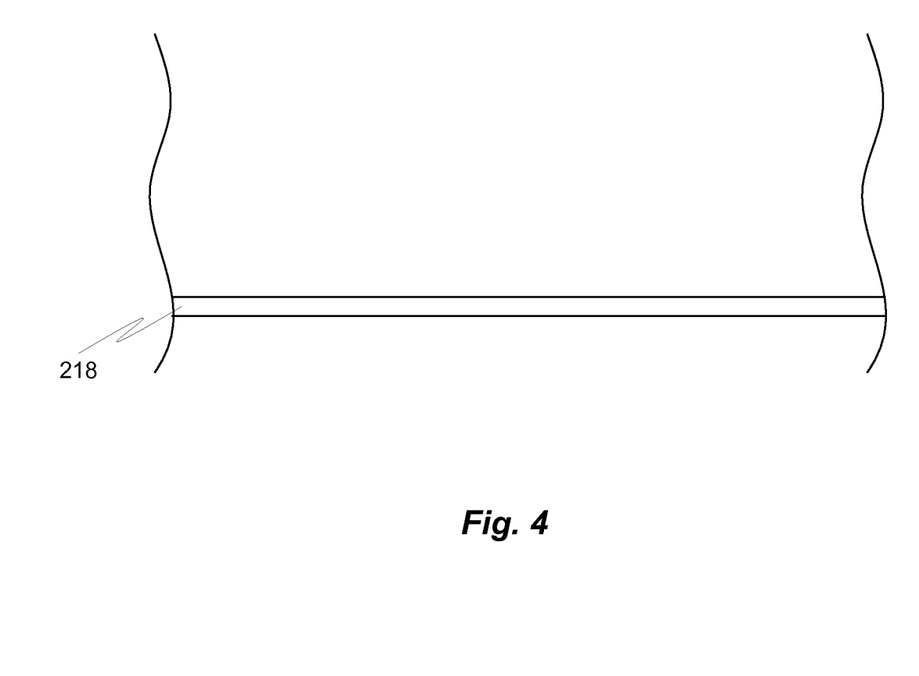
FIG. 4 depicts a partial cross-sectional view of a microfluidic channel at a first step of manufacturing in accordance with at least some embodiments of the present invention.

Referring now to FIGS. 3-9, an exemplary method of constructing a microfluidic device 100 will be described in accordance with at least some embodiments of the present invention. The method begins by providing a substrate 218 (FIG. 4; step 304). Thereafter, the substrate 218 is functionalized (step 308). In this step, the substrate 218 may be treated with octadecyltrichlorosilane (OTS), thereby creating a monolayer of OTS on the upper surface of the substrate 218. Methods of rendering substrates, such as glass substrates, hydrophobic are well known in the art. Methods of functionalizing the substrate 218 include, without limitation, rendering the substrate hydrophobic, hydrophilic, reactive (via amine or carboxylic acid groups), or some other chemistry. In particular, different surface chemistries may allow different molecules to be patterned in a specific configuration. In one embodiment, silane chemistries may be used on glass substrates.

Figure 5:
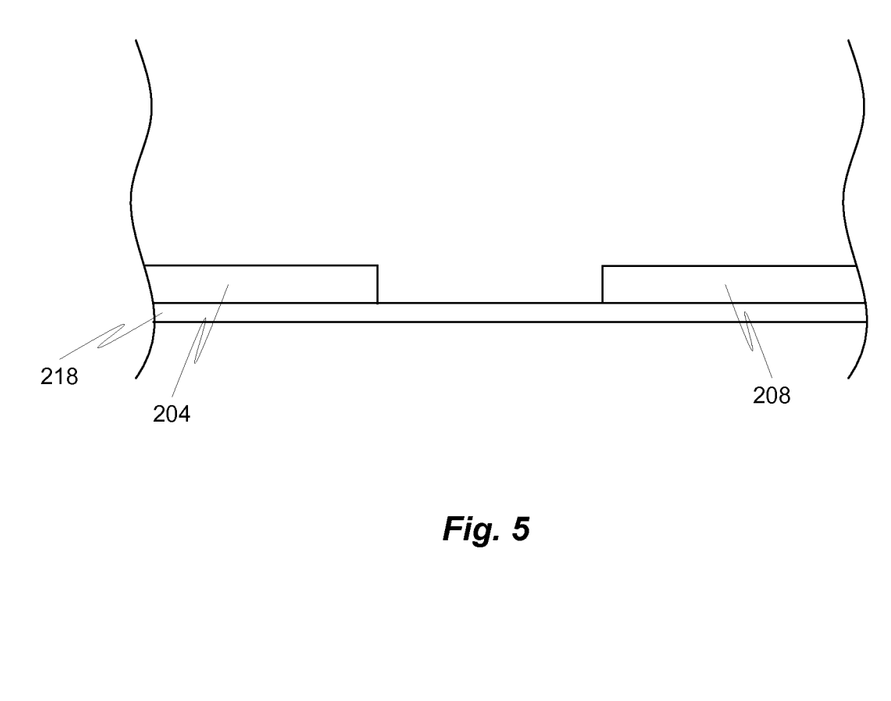
FIG. 5 depicts a partial cross-sectional view of a microfluidic channel at a second step of manufacturing in accordance with at least some embodiments of the present invention.

After the substrate 218 has been functionalized, the method continues by forming the prothrombotic surface 132, which will ultimately include the clot forming area 136 (FIG. 5; step 312). In particular, the BSA may be provided as the first 204 and second 208 surface. The void between the first 204 and second 208 surfaces generally corresponds to the channel in which the prothrombotic structure 120a or 120b will be created. This void may be created by providing a masking layer on the substrate 218 prior to applying the BSA to the substrate 218. After the BSA has been provided, the masking layer may be removed from the substrate 218, thereby exposing the void between the first 204 and second 208 areas.

Figure 6:
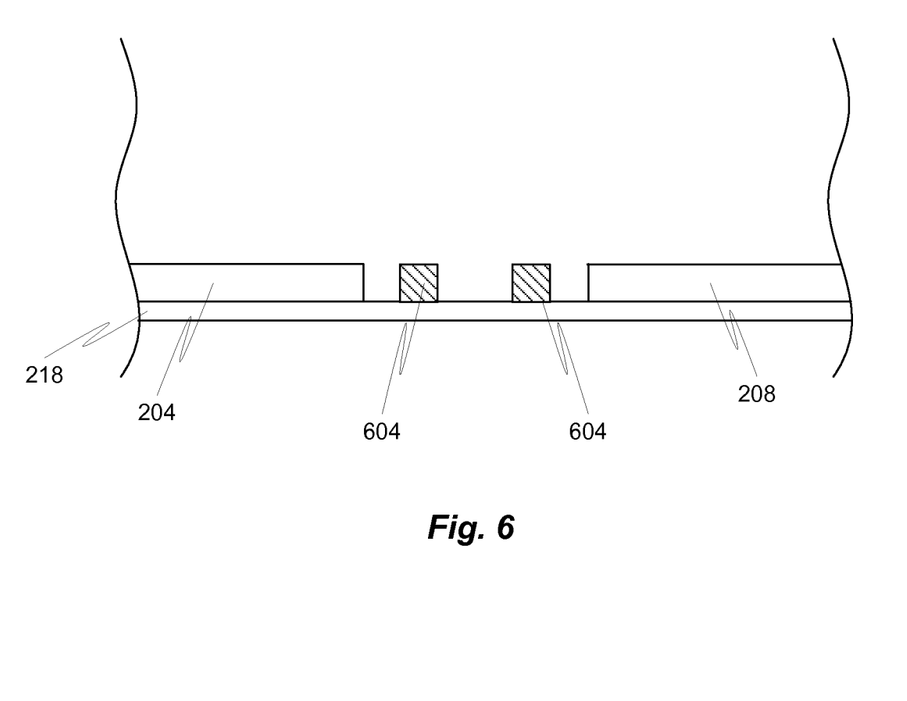
FIG. 6 depicts a partial cross-sectional view of a microfluidic channel at a third step of manufacturing in accordance with at least some embodiments of the present invention.

After the BSA has been laid down on the substrate 218, the method continues by positioning a pillar-creating structure 604 on the substrate 218, particularly in the clot forming area 136 (FIG. 6; step 316). This pillar-creating structure 604 may comprise a PDMS structure that is formed to have pillars or structures of a size substantially the same as a desired size of the structures of tissue factor 216. In some embodiments, the pillar-creating structure 604 comprises a single structure having a plurality of posts extending therefrom which touch the surface of the substrate 218 in the clot forming area 136. In other embodiments, the pillar-creating structure 604 comprises a plurality of distinct posts placed on the surface of the substrate 218 in the clot forming area 136. The posts of the pillar-creating structure 604 are generally used as masks to prevent collagen from adhering to the substrate 218 during subsequent manufacturing steps.

Figure 7:
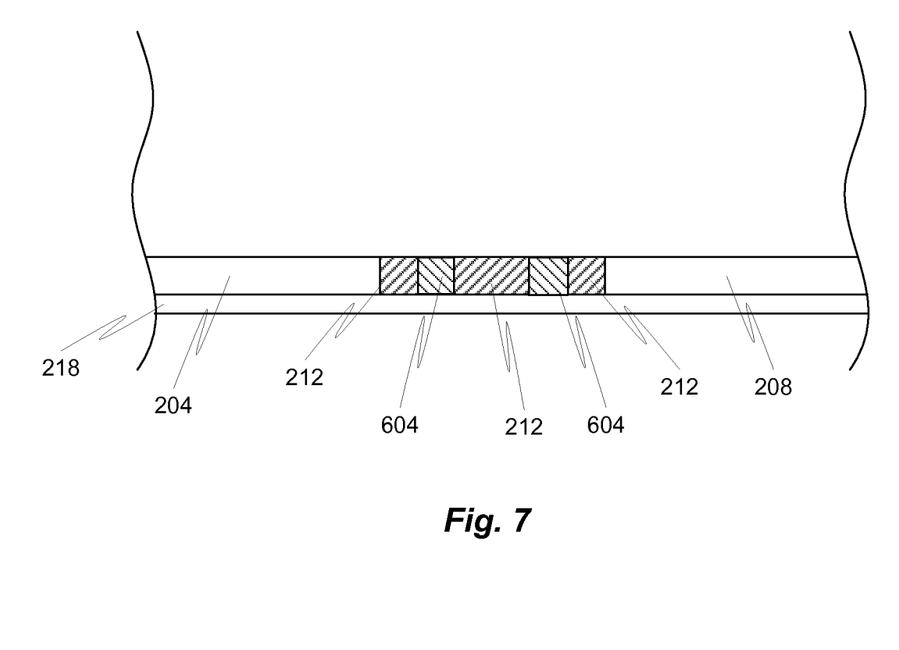
FIG. 7 depicts a partial cross-sectional view of a microfluidic channel at a fourth step of manufacturing in accordance with at least some embodiments of the present invention.

Once the pillar-creating structure 604 is in place, the method continues by adding a collagen material 212 to the substrate 218 in the clot forming area 136 (FIG. 7; step 320). The collagen material 212 interacts with the exposed surface of the substrate 218 and eventually adheres thereto. Also, the collagen material 212 does not adhere to the substrate 218 in areas where the pillar-creating structure 604 is present. In some embodiments, the collagen material 212 may be added to the substrate 218 by submerging the substrate 218 in a collagen bath for a sufficient time to ensure that an even layer of collagen material 212 has been created in the clot forming area 136.

Figure 8:
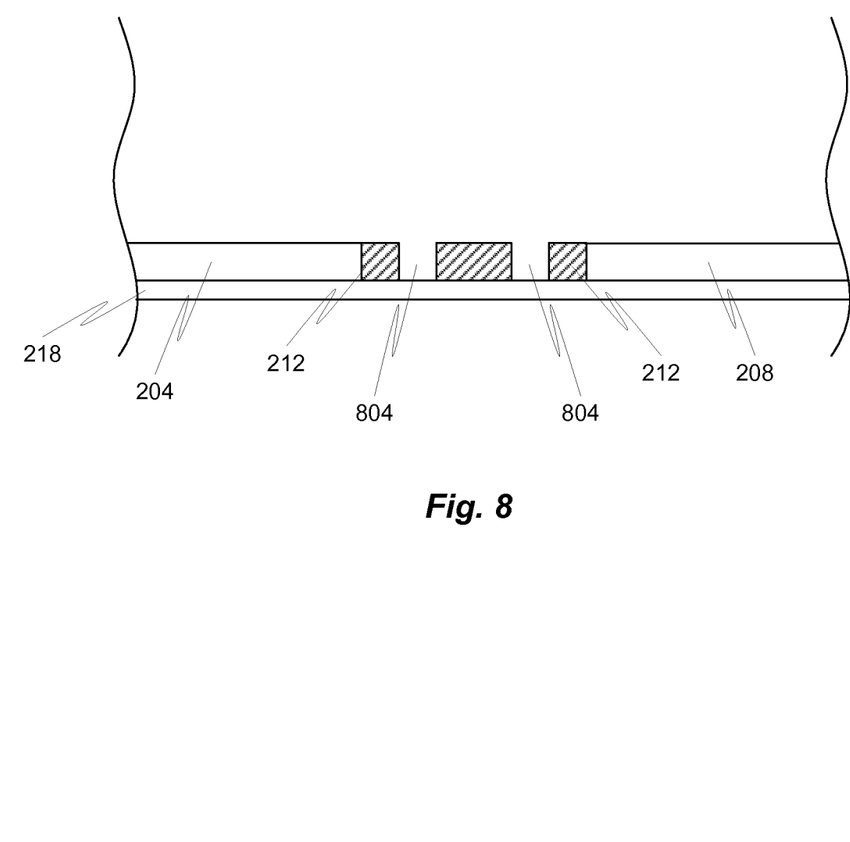
FIG. 8 depicts a partial cross-sectional view of a microfluidic channel at a fifth step of manufacturing in accordance with at least some embodiments of the present invention.
Figure 9:
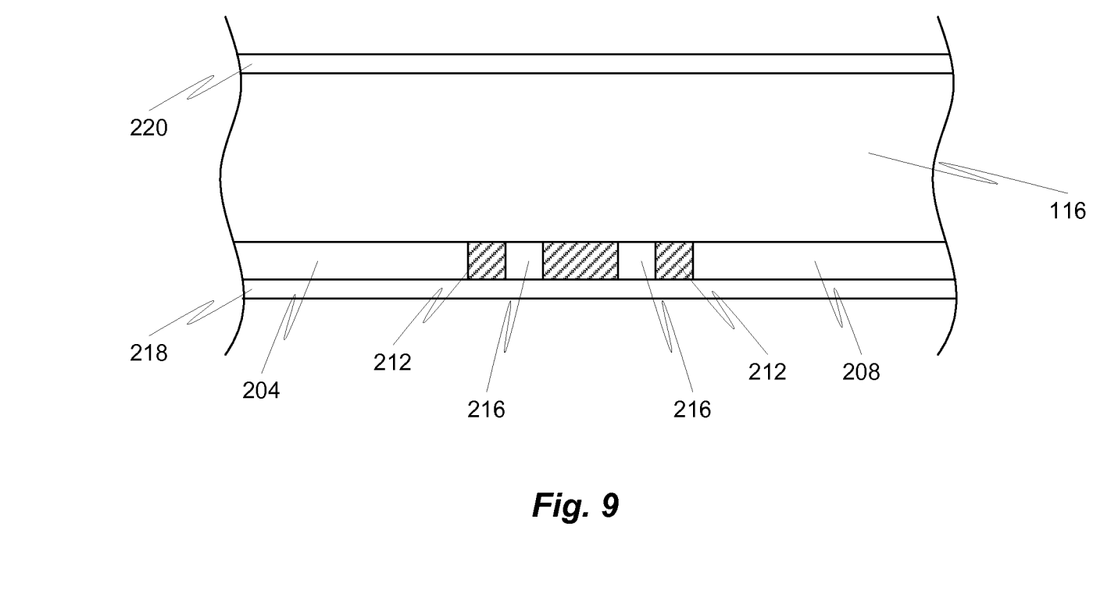
FIG. 9 depicts a partial cross-sectional view of a microfluidic channel at a sixth step of manufacturing in accordance with at least some embodiments of the present invention.

Thereafter, the method continues by removing the pillar-creating structure 604 from the substrate 218 to reveal collagen voids 804 (FIG. 8; step 324). The lipid 216 is then added to the substrate 218 to fill the collagen voids 804, thereby creating the structures of tissue factor 216 (FIG. 9; step 328). Again, the lipid 216 can be added to the substrate 218 by submerging the substrate 218 into a lipid bath until the collagen voids 804 have been sufficiently filled and a substantially smooth lower surface of the microfluidic channel 116 has been created (e.g., substantially smooth surface is created between the first area 204 of BSA, the collagen material 212, the structures of tissue factor 216, and the second area 208 of BSA).

At this point, the creation of the prothrombotic structure 120a or 120b is complete. As can be appreciated by one skilled in the art, although the method of creating only one prothrombotic structure 120a or 120b was depicted and described, multiple prothrombotic structures 120a and 120b (or more) can be created at substantially the same time on a single substrate 218 by following the steps described above. Accordingly, multiple prothrombotic structures 120a and 120b can be created at substantially the same time, thereby reducing the amount of time required to construct a microfluidic device 100.

As an alternative to creating pillar structures 604, embodiments of the present invention are capable of utilizing laminar flow patterning in which both protein and lipid solutions are introduced simultaneously under flow to the substrate 218 to form lanes (i.e., alternating lanes of protein-lipid-protein-lipid-protein-etc. across the width of the clot forming area 136) Accordingly, rather than creating pillar structures in the clot forming area 136, lane structures that have a long axis substantially parallel to the fluid flow direction are created. In the event that laminar flow patterning is employed to create lane structures, the laminar flow patterning step may replace or augment one or more of steps 316, 320, 324, and 328.

Once the prothrombotic structure(s) 120a and/or 120b are in place, the method continues by positioning a microfluidic channel structure or lid 220 across the clot forming area(s) 136 (FIG. 9; step 332). As discussed in connection with FIG. 1, the microfluidic channels 116 may be created within a PDMS material and may be positioned to intersect the prothrombotic structure(s) 120a and/or 120b at only selected locations, thereby controlling the amount of clot forming that is induced when blood is flowed through the microfluidic channels 116.

At this point, a microfluidic device 100 has been created. In accordance with at least some embodiments of the present invention, the microfluidic device 100 may be hygienically sealed in a sterile environment (e.g., hermetic plastic package) (step 336) such that the microfluidic device 100 can be distributed as a clot testing kit to medical personnel and other interested parties (step 340). One possible complication with a kit that may need to be addressed is the fact that lipids must be stored in an aqueous environment, in other words, they can't be dried out. Accordingly, prior to hermetically sealing the microfluidic device 100 in a sterile environment, an aqueous solution may be injected into the hermetic packaging prior to final sealing. This will enhance the shelf life of the kit as well as enhance its ability to be distributed great distances away from its source of manufacture.

In other embodiments, a vacuum source can be utilized to vacuum seal the substrate 218 to the lid 220. Such a device 100 can be used in various testing facilities. Moreover, the vacuum assisted sealing of the lid 220 and substrate 218 is a reversible bonding technique which may allow testing personnel to reposition the lid 220 relative to the substrate 218 without damaging either component.

In accordance with at least some embodiments of the present invention, once the microfluidic device 100 has been prepared, one or more blood samples can be passed through the microfluidic channels 116 of the device 100 to analyze bleeding and thrombotic disorders, dosing anticoagulant and antiplatelet drugs, tracking the effects of pharmacological interventions on thrombosis, and the like. In particular, platelet flow can be analyzed and platelet adhesion can be quantified in any number ways. As one example, platelet labeling and detection schemes can be employed whereby blood platelets are fluorescently labeled with a small molecule or platelet specific antibody that is fluorescently visible. As the blood with the labeled platelets flows through the microfluidic channels 116 of the device 100, and more specifically across the clot forming areas 136 in the channels 116, the number (specific or relative) of platelets that have adhered to and/or around the clot forming area 136 may be observed. Such observations can be made in real-time with fluorescent imaging devices, cameras, recording devices, and the like, or after an experiment has been performed. Real-time and/or post-testing analysis can help yield quantifiable results as to the number of platelets that have adhered to the clot forming area 136, which can then be correlated to standard test results or other variables to determine whether the patient is prone to excessive bleeding or the like.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiments described hereinabove are further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A microfluidic device, comprising:
   at least one microfluidic channel; and
   at least one prothrombotic surface provided in the at least one microfluidic channel, wherein the at least one prothrombotic surface comprises a cell adhesive protein and at least one structure, wherein the at least one structure consists essentially of a protein embedded in a lipid that induces coagulation, wherein the cell adhesive protein and the at least one structure are in distinct regions of the at least one prothrombotic surface.

2. The device of claim 1, wherein the cell adhesive protein is selected from the group consisting of collagen and von Willebrand factor.

3. The device of claim 2, wherein the cell adhesive protein is collagen.

4. The device of claim 2, wherein the cell adhesive protein is von Willebrand factor.

5. The device of claim 1, wherein the the protein embedded in the lipid is tissue factor.

6. The device of claim 5, wherein the tissue factor is interspersed in a predetermined geometry throughout the cell adhesive protein.

7. The device of claim 6, wherein a surface area of the at least one prothrombotic surface is at least ten times smaller than a surface area of the at least one microfluidic channel.

8. The device of claim 6, wherein a surface area of the at least one prothrombotic surface is at least one hundred times smaller than a surface area of the at least one microfluidic channel.

9. The device of claim 5, wherein the at least one structure has a diameter of between about 10 microns to about 100 microns.

10. The device of claim 5, wherein the at least one structure has a diameter of about 10 microns.

11. The device of claim 1, wherein the at least one structure are provided in the cell adhesive protein and wherein each of the at least one structure have a width of less than 100 microns.

12. The device of claim 1, wherein the at least one prothrombotic surface comprises a surface area of less than 10,000 square microns.

13. The device of claim 1, further comprising:
a first antithrombotic region, wherein the first antithrombotic region is in the at least one microfluidic channel and positioned in a region proceeding a clot forming region in the at least one prothrombotic surface; and
a second antithrombotic region, wherein the second antithrombotic region is in the at least one microfluidic channel and positioned in a region following the clot forming region in the at least one prothrombotic surface.

14. The device of claim 13, wherein the first antithrombotic region and the second antithrombotic region comprise a passivity protein, wherein the passivity protein does not induce platelet adhesion or coagulation cascade.

15. The device of claim 14, wherein the first antithrombotic region comprises bovine serum albumin.

16. The device of claim 1, wherein the at least one prothrombotic surface has a cross sectional area of about 50 microns by about 250 microns.

17. The device of claim 1, wherein the ratio of the cell adhesive protein and the at least one structure in the at least one prothrombic surface is less than 1:1.

18. A microfluidic device made by a method, the method comprising:
providing a substrate;
creating at least one prothrombotic surface on the substrate, wherein the at least one prothrombotic surface comprises a cell adhesive protein and at least one structure, wherein the at least one structure consists essentially of a protein embedded in a lipid that induces coagulation, wherein the cell adhesive protein and the at least one structure are in distinct regions of the at least one prothrombotic surface; and
establishing at least one microfluidic channel which intersects at least a portion of the at least one prothrombotic surface.

19. A microfluidic channel through which blood is capable of flowing, the channel comprising:
at least one prothrombotic surface provided as a part of at least a portion of one surface in the channel, wherein the at least one prothrombotic surface comprises a cell adhesive protein and at least one structure, wherein the at least one structure consists essentially of a protein embedded in a lipid that induces coagulation, wherein the cell adhesive protein and the at least one structure are in distinct regions of the at least one prothrombotic surface, wherein a surface area of the at least one prothrombotic surface is at least one hundred times smaller than a surface area of the at least one microfluidic channel, wherein the at least one structure are provided in the collagen and wherein each of the at least one structures have a surface area of less than 100 microns, wherein the protein embedded in the lipid is tissue factor, and wherein the cell adhesive protein is selected from the group consisting of collagen and von Willebrand factor.

20. A kit for measuring clotting characteristics of blood, the kit comprising:
a hermetically sealed microfluidic device, the microfluidic device comprising at least one microfluidic channel and at least one prothrombotic surface provided in the at least one microfluidic channel, wherein the at least one prothrombotic surface comprises a cell adhesive protein and at least one structure, wherein the at least one structure consists essentially of a protein embedded in a lipid that induces coagulation, wherein the cell adhesive protein and the at least one structure are in distinct regions of the at least one prothrombotic surface.

* * * * *